US010145768B2

(12) United States Patent
Ohmae et al.

(10) Patent No.: US 10,145,768 B2
(45) Date of Patent: Dec. 4, 2018

(54) SMEAR PREPARATION APPARATUS AND SMEAR PREPARATION METHOD

(71) Applicant: SYSMEX CORPORATION, Kobe-shi, Hyogo (JP)

(72) Inventors: Yuichiro Ohmae, Kobe (JP); Seiya Shinabe, Kobe (JP); Kosuke Sekizuka, Kobe (JP)

(73) Assignee: SYSMEX CORPORATION, Kobe-shi (JP)

( * ) Notice: Subject to any disclaimer, the term of this patent is extended or adjusted under 35 U.S.C. 154(b) by 0 days.

(21) Appl. No.: 15/599,539

(22) Filed: May 19, 2017

(65) Prior Publication Data

US 2017/0254731 A1    Sep. 7, 2017

Related U.S. Application Data

(63) Continuation of application No. PCT/JP2015/005878, filed on Nov. 26, 2015.

(30) Foreign Application Priority Data

Nov. 26, 2014    (JP) .................................. 2014-239087

(51) Int. Cl.
*G01N 1/00*    (2006.01)
*G01N 1/31*    (2006.01)
(Continued)

(52) U.S. Cl.
CPC ............... *G01N 1/312* (2013.01); *C12M 3/00* (2013.01); *G01N 1/28* (2013.01); *G01N 1/2813* (2013.01);
(Continued)

(58) Field of Classification Search
CPC ........................................................ G01N 1/00
See application file for complete search history.

(56) References Cited

U.S. PATENT DOCUMENTS 2,623,301 A    12/1952    Weiskopf
5,078,969 A    1/1992    Bacus
(Continued)

FOREIGN PATENT DOCUMENTS

DE    102013210995 A1    12/2014
JP    S58-155360 A    9/1983
(Continued)

OTHER PUBLICATIONS

International Search Report of PCT/JP2015/005878 dated Feb. 16, 2016.

*Primary Examiner* — Jyoti Nagpaul
(74) *Attorney, Agent, or Firm* — Metrolexis Law Group, PLLC

(57) ABSTRACT

The time period necessary for a staining process is shortened, and the apparatus is downsized. This smear preparation apparatus includes: a staining vessel for storing a staining liquid therein so as to allow a plurality of glass slides each having a sample smeared thereon to be immersed therein; and a transfer unit for holding and transferring each glass slide. The staining vessel includes a plurality of first holders configured to hold the glass slides. The staining vessel is configured such that a plurality of glass slides held by a plurality of the first holders are immersed in the stored staining liquid, and the transfer unit is configured to put in/take out the glass slides one by one with respect to a plurality of the first holders of the staining vessel.

33 Claims, 11 Drawing Sheets

(51) Int. Cl.
    *G01N 1/28*         (2006.01)
    *G01N 1/30*         (2006.01)
    *G01N 33/48*       (2006.01)
    *C12M 3/00*        (2006.01)
    *G01N 35/00*       (2006.01)

(52) U.S. Cl.
    CPC .............. *G01N 1/30* (2013.01); *G01N 33/48* (2013.01); *G01N 35/00029* (2013.01); *G01N 35/00069* (2013.01); *G01N 35/0099* (2013.01); *G01N 35/00732* (2013.01); *G01N 2035/00039* (2013.01); *G01N 2035/00138* (2013.01)

(56) References Cited

U.S. PATENT DOCUMENTS

| | | |
|---|---|---|
| 5,215,718 A | 6/1993 | Katzer et al. |
| 5,779,982 A | 7/1998 | Acta et al. |
| 6,080,363 A | 6/2000 | Takahashi et al. |
| 6,319,470 B1 | 11/2001 | Lefevre et al. |
| 2009/0110597 A1* | 4/2009 | Ljungmann ............ G01N 1/312 422/62 |

FOREIGN PATENT DOCUMENTS

| | | |
|---|---|---|
| JP | H02-150549 U | 12/1990 |
| JP | H04-027380 A | 1/1992 |
| JP | H08-043380 A | 2/1996 |
| JP | H08-271390 A | 10/1996 |
| JP | H09-043118 A | 2/1997 |
| JP | H10-090144 A | 4/1998 |
| JP | 2000-074803 A | 3/2000 |
| JP | 2001-021468 A | 1/2001 |
| JP | 2007-183293 A | 7/2007 |
| WO | WO94023326 A1 | 10/1994 |

* cited by examiner

SMEAR PREPARATION APPARATUS AND SMEAR PREPARATION METHOD

CROSS REFERENCE TO RELATED APPLICATION

This application is a Continuation of International Application No. PCT/JP2015/005878, filed on Nov. 26, 2015, which in turn claims the benefit of Japanese Patent Application No. 2014-239087 filed on Nov. 26, 2014, the disclosures of which Applications are incorporated by reference herein.

BACKGROUND OF THE INVENTION

Field of the Invention

The present invention relates to a smear preparation apparatus and a smear preparation method.

Description of the Background Art

Japanese Laid-Open Patent Publication No. H10-90144 discloses a smear preparation apparatus provided with: a staining basket which accommodates a plurality of glass slides; a transfer mechanism for hanging and moving the staining basket; and a liquid storage container for storing a staining liquid therein. In the smear preparation apparatus of Japanese Laid-Open Patent Publication No. H10-90144, the transfer mechanism immerses the staining basket accommodating a plurality of glass slides, into a staining liquid in the liquid storage container, whereby the plurality of glass slides are stained at one time.

The smear preparation apparatus of Japanese Laid-Open Patent Publication No. H10-90144 has the following problems. That is, since a plurality of glass slides are stained at one time in the staining basket, and staining operation is not performed until a plurality of glass slides are accumulated in the staining basket, the time period turn around time) from the tune when an order of smear preparation is generated until the smear is prepared becomes long. In addition, there is also a problem that since staining is performed by using the staining basket, the size of the apparatus is increased.

SUMMARY OF THE INVENTION

A smear preparation apparatus according to a first aspect of the present invention includes: a staining vessel for storing a staining liquid therein so as to allow a plurality of glass slides each having a sample smeared thereon to be immersed therein; and a transfer unit for holding and transferring each glass slide, wherein the staining vessel includes a plurality of first holders configured to hold the glass slides, the staining vessel is configured such that a plurality of glass slides held by a plurality of the first holders are immersed in the stored staining liquid, and the transfer unit is configured to put in/take out the glass slides one by one with respect to a plurality of the first holders of the staining vessel.

A smear preparation method according to a second aspect of the present invention includes: storing a staining liquid so as to immerse, in a staining vessel including a plurality of first holders configured to hold glass slides each having a sample smeared thereon, a plurality of the glass slides held by a plurality of the first holders; gripping and transferring, by a transfer unit, each glass slide to the staining vessel; and putting in/taking out the glass slides one by one, by the transfer unit, with respect to a plurality of the first holders of the staining vessel.

According to the present invention, the time period necessary for a staining process is shortened, and the apparatus can be downsized.

These and other objects, features, aspects, and effects of the present invention will become more apparent from the following detailed description when taken in conjunction with the accompanying drawings.

DESCRIPTION OF THE PREFERRED EMBODIMENTS

Hereinafter, embodiments are described with reference to the drawings.

With reference to FIG. 1 to FIG. 6, a smear preparation apparatus 100 according to the present embodiment is described.

Outline of Smear Preparation Apparatus

The smear preparation apparatus 100 is an apparatus for automatically creating a smear by performing, on a sampling glass slide 10, a smearing process of smearing a sample, and a process of staining the glass slide 10 having the sample smeared thereon. The sample is blood, for example.

Figure 1:
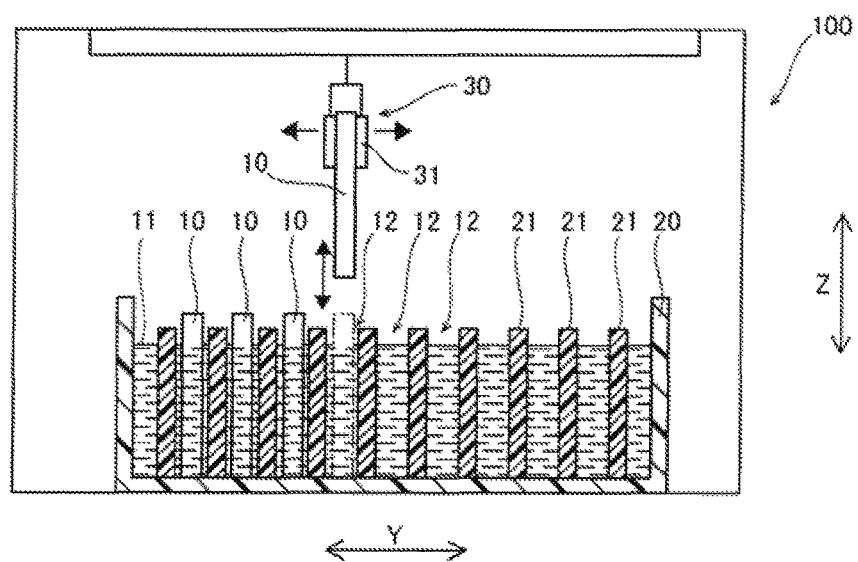
FIG. 1 is a schematic diagram showing the outline of a smear preparation apparatus according to one embodiment.

As shown in FIG. 1, the smear preparation apparatus 100 includes a staining vessel 20 and a transfer unit 30.

The staining vessel 20 is formed in a container shape, and can store therein a staining liquid 11 so as to allow a glass slide 10 having a sample smeared thereon to be immersed therein. The staining vessel 20 is formed in a container shape, and can store a staining liquid 11 therein. The staining vessel 20 includes a plurality of first holders 21 configured to hold the glass slides 10. The first holders 21 form insertion regions 12 into each of which a glass slide 10 can be inserted. A staining process is performed by immersing, in the staining liquid 11 for a predetermined time period, the glass slides 10 held by the first holders 21 in the staining vessel 20.

As the configuration of the plurality of the first holders 21 for forming the insertion regions 12, a variety of configurations can be employed. For example, the plurality of the first holders 21 may be members arranged with an interval therebetween in a predetermined direction, as shown in FIG. 1. In this case, an insertion region 12 can be formed between adjacent first holders 21. Other than this, the first holders 21 may each be configured by horizontally disposing, at a predetermined height position in the staining vessel 20, a plate member (not shown) provided with a slit-like first holder into which a glass slide 10 can be inserted, for example. In this case, an insertion region 12 can be formed in the slit-like first holder. It is sufficient that the number of first holders 21 is a plural number, and the number of first holders 21 can be set in accordance with the configuration of the apparatus.

The transfer unit 30 is provided in order to grip and transfer a glass slide 10 having a sample smeared thereon. The transfer unit 30 is configured to put in/take out the glass slides 10 one by one with respect to a plurality of the first holders 21 of the staining vessel 20. That is, the transfer unit 30 can set the glass slides 10 one by one into the insertion regions 12 of the first holders 21.

Also as the configuration of the transfer unit 30 for putting in/taking out the glass slides 10 one by one with respect to the respective first holders 21, various configurations can be employed. For example, as shown in FIG. 1, the transfer unit 30 is a 3-axis orthogonal robot that can move in the horizontal direction and the up-down direction (Z direction), and that includes a hand 31 for grasping a glass slide 10. The transfer unit 30 may be able to move only one of the horizontal direction and the up-down direction, and the staining vessel 20 may be able to move in the other of the horizontal direction and the up-down direction. For example, the hand 31 may be realized as an open/close mechanism that can nip and grip a glass slide 10, or a suction mechanism that suctions and grips a predetermined portion of a glass slide 10.

With the above configuration, the transfer unit 30 sets the glass slides 10 one by one to the first holders 21 of the staining vessel 20 in which the staining liquid 11 is stored, whereby the staining process for the glass slides 10 can be performed. Accordingly, at the time point when individual glass slides 10 get ready, the staining process can be quickly started for the glass slides 10 one by one. Thus, differently from a configuration in which a plurality of glass slides set in a staining basket are stained at one time, there is no need to wait for the staining operation to be started until a plurality of glass slides 10 are accumulated in the staining basket. As a result, the time period necessary for the staining process can be shortened.

Since the plurality of the first holders 21 use the staining liquid 11 in common, the staining and washing steps can be simplified, compared with a case where staining is performed by using a slide container that holds a single glass slide. The reason is as follows. In a case where staining is performed by using a slide container that holds a single glass slide, the slide container needs to be washed each time one glass slide is stained, and thus, pouring and discharging of the staining liquid and the washing liquid need to be performed each time. However, in the case of the present embodiment, a plurality of glass slides held by a plurality of the first holders 21 use the staining liquid 11 in common, and thus, pouring and discharging of the staining liquid and the washing liquid need not be performed each time a slide is stained, and thus, steps can be simplified. In addition, in a case where staining is performed by using a slide container that holds a single glass slide, staining is performed by putting a small amount of the staining liquid into a slide container which is small compared with the staining vessel 20 of the present embodiment. In the case of the present embodiment, a configuration is employed in which a plurality of glass slides held by a plurality of the first holders are immersed in the stored staining liquid, and thus, variation in the staining degree among the plurality of glass slides depending on the state of the slide container such as due to smudges can be suppressed.

Since the transfer unit 30 is configured to put in/take out the glass slides 10 one by one with respect to a plurality of the first holders 21, there is no need to move a large member such as a staining basket that can accommodate a plurality of glass slides 10. Accordingly, the transfer unit 30 and the staining vessel 20 can be downsized, and the space necessary for moving the transfer unit 30 can be reduced. As a result, according to the smear preparation apparatus 100, the time period necessary for the staining process can be shortened and the apparatus can be downsized.

Details of Configuration of Smear Preparation Apparatus

Hereinafter, with reference to FIG. 2 and thereafter, specific configurations of a preferred embodiment of the smear preparation apparatus 100 shown in FIG. 1 are described.

Figure 2:
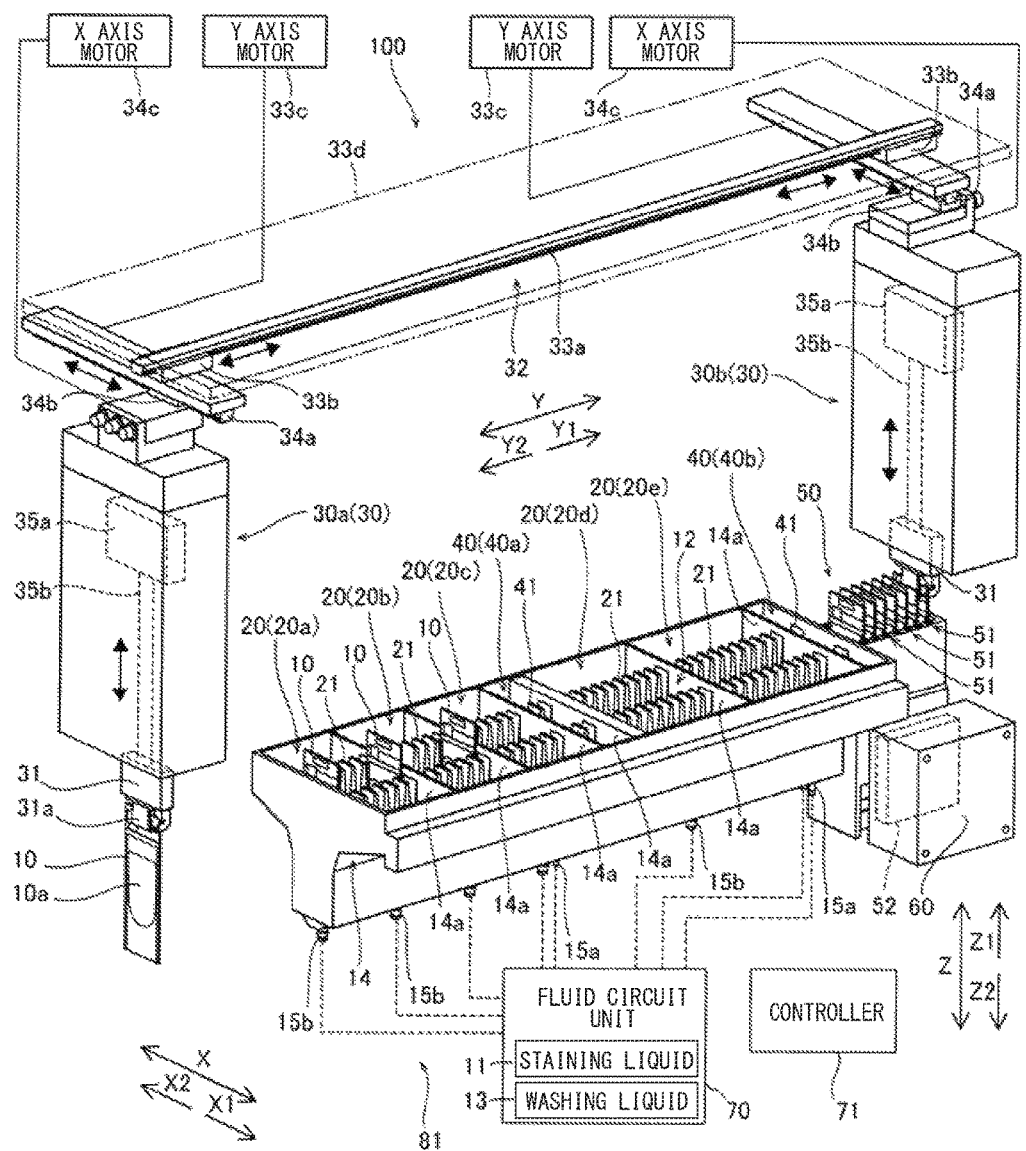
FIG. 2 is a perspective view showing specific configurations of a staining vessel and a transfer unit of the smear preparation apparatus according to one embodiment.

As shown in FIG. 2, the smear preparation apparatus 100 may further include a washing vessel 40, a drying vessel 50, and an air-sending unit 60. The transfer unit 30 includes a first transfer unit 30a and a second transfer unit 30b. The smear preparation apparatus 100 includes: a fluid circuit unit 70 configured to respectively supply/discharge the staining liquid 11 and a washing liquid 13 to/from the staining vessel 20 and the washing vessel 40; and a controller 71 configured to control the transfer unit 30, the air-sending unit 60, and the like. The controller 71 is a computer that includes a CPU and a memory not shown.

In the following, the width direction of the glass slide 10 to be inserted in the staining vessel 20 (i.e., the width direction of the insertion region 12) is defined as an X direction, and the arrangement direction of the glass slides 10 to be inserted in the staining vessel 20 (that is, the thickness direction of the insertion region 12) is defined as a Y direction. The up-down direction which is the direction along which the glass slide 10 is inserted is defined as a Z direction.

Preferably, the staining vessel 20 includes a first staining vessel 20a for storing a first staining liquid therein, and a second staining vessel 20b for storing a second staining liquid therein, and the staining vessel 20 includes a separation member 14a for separating the first staining vessel 20a and the second staining vessel 20b from each other. FIG. 2 shows an example in which the staining vessel 20 includes five staining vessels 20, i.e., the first staining vessel 20a to a fifth staining vessel 20e. The first staining vessel 20a, the second staining vessel 20b, and the third staining vessel 20c are integrally formed while being separated from one another by separation members 14a. Furthermore, the fourth staining vessel 20d and the fifth staining vessel 20e are integrally formed while being separated from each other by a separation member 14a. Since the first staining vessel 20a to the fifth staining vessel 20e are integrally formed while being separated from one another by the separation members 14a in this manner, even in a case where the staining process is performed by using a plurality of kinds of the staining liquids 11, the first staining vessel 20a to the fifth staining vessel 20e can be integrally formed as a whole. As a result, when compared with a case where each staining vessel is individually formed, the configuration of the apparatus can be simplified.

The washing vessel 40 is provided in order to store therein the washing liquid 13 so as to allow the glass slides 10 to be immersed therein. As the configuration of the washing vessel 40, a configuration common to the staining vessel 20 can be employed. That is, the washing vessel 40 includes a plurality of second holders 41 each similar to the first holder 21, and can hold the glass slides 10 in the second holders 41 configured to hold glass slides 10. The transfer unit 30 is configured to put in/take out the glass slides 10 one by one with respect to the plurality of second holders 41 of the washing vessel 40. Accordingly, in a washing process step after the staining process, at the time point when individual glass slides 10 get ready, the washing process can be quickly started for the glass slides 10 one by one. As a result, there is no need to wait for the washing operation to be started until a plurality of glass slides 10 are accumulated. Thus, the time period necessary for the washing process can be shortened.

Figure 3:
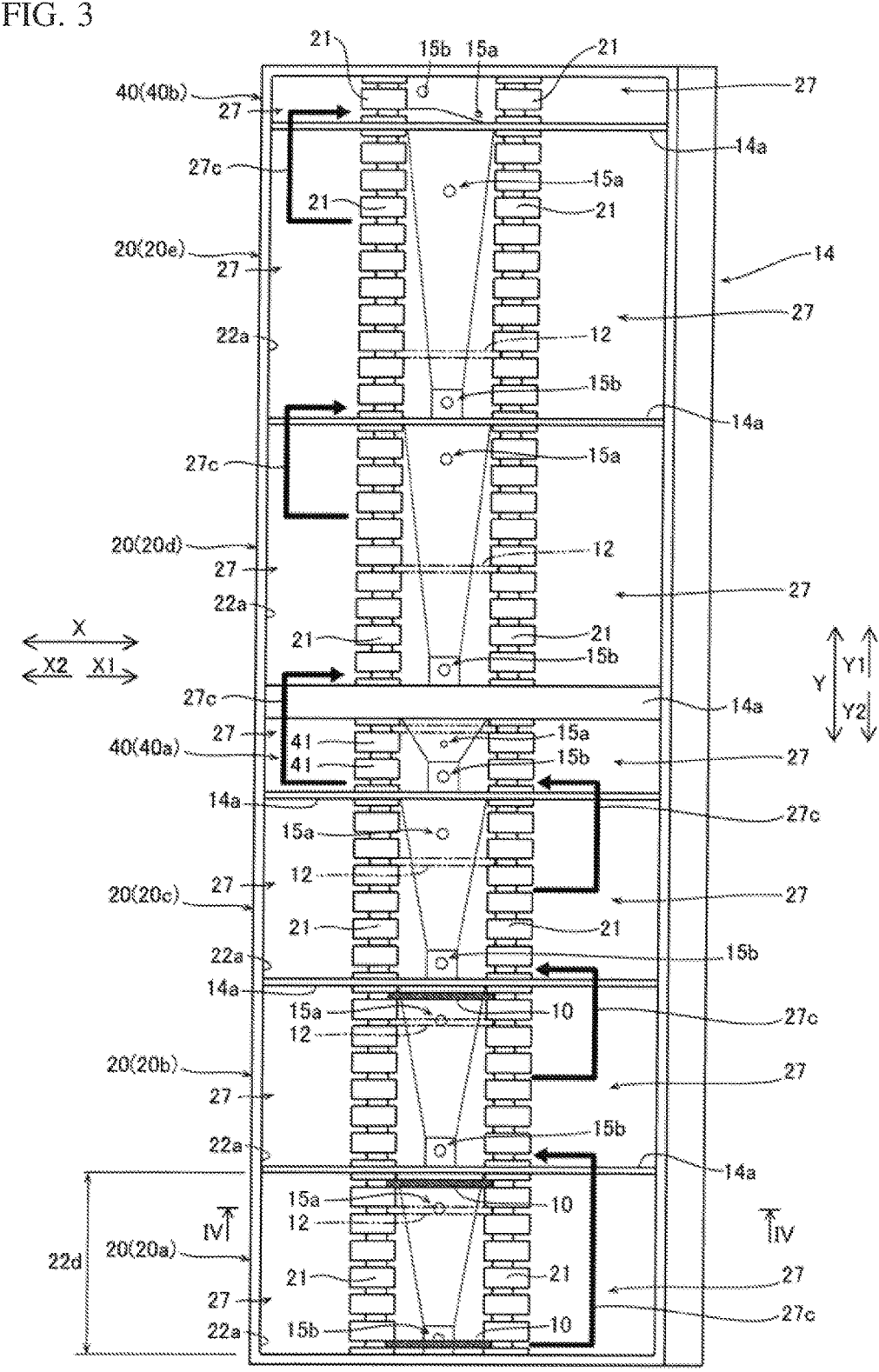
FIG. 3 is a schematic top view of the staining vessel and the washing vessel shown in FIG. 2.

As shown in FIG. 3, the washing vessel 40 includes a first washing vessel 40a and a second washing vessel 40b separated by the separation members 14a. In addition, five staining vessels 20 of the first staining vessel 20a to the fifth staining vessel 20e, and two washing vessels 40 of the first washing vessel 40a and the second washing vessel 40b are integrally formed in a single structure 14.

That is, the single structure 14 includes a large number of first holders 21 and second holders 41 arranged in the Y direction. The single structure 14 is provided with a total of six plate-like separation members 14a that separate the vessels from one another at predetermined positions in the Y direction. Via these separation members 14a, five staining vessels 20 and two washing vessels 40 are integrally formed so as to be arranged in the Y direction in the single structure 14. The numbers of the staining vessels 20 and the washing vessels 40 may be set to numbers in accordance with the number of steps of the staining process. The single structure 14 is preferably formed from a resin material or the like that has chemical resistance and that is easy to be washed.

The five staining vessels 20 and the two washing vessels 40 are separated from one another by the separation members 14a, and thus, do not allow liquid to flow thereamong. Each of the staining vessels 20 and the washing vessels 40 are provided with a supply port 15a for supplying a liquid, and with a discharge port 15b for discharging a liquid, individually. Accordingly, the staining vessels 20 and the washing vessels 40 can each store the staining liquid 11 or the washing liquid 13 of a kind different from one another. In the staining process for the glass slide 10, a plurality of kinds of the staining liquids 11 are used. All of the staining liquid 11 in each vessel is replaced after a previously-set predetermined number of glass slides 10 have been stained.

The staining vessels 20 and the washing vessels 40 are arranged, in the order from the Y2 direction side, the first staining vessel 20a, the second staining vessel 20b, the third staining vessel 20c, the first washing vessel 40a, the fourth staining vessel 20d, the fifth staining vessel 20e, and the second washing vessel 40b. The glass slides 10 are transferred into the vessels in the order starting at the first staining vessel 20a at the Y2 direction side, and are immersed for a predetermined set time period in the staining liquid 11 or the washing liquid 13 stored in the corresponding vessels, thereby being processed. The set time period for the process performed in each vessel is different depending on the kind of the staining liquid 11 or the washing liquid 13 stored in the vessel, and is set to a time period necessary for processing the glass slides 10.

The number of first holders 21 of each staining vessel 20 and the number of second holders 41 in each washing vessel 40 (that is, the number of insertion regions 12) are each set to a number corresponding to the set time period for processing the glass slides 10. The number of first holders 21 and the number of second holders 41 are preferably determined in accordance with the carry-in time interval of the glass slides 10 as a specification of the smear preparation apparatus 100, and the length of the set time period that is set for processing the glass slides 10 in each vessel. That is, when the carry-in time interval is defined as A and a set time period for a vessel is defined as B, the first holders 21 and the second holders 41 are provided such that at least B/A glass slides 10 can be inserted in that vessel. Preferably, the first holders 21 and the second holders 41 are provided by a number greater than B/A.

In a case of a process step having a long set time period, an identical kind of the staining liquid 11 may be stored in a plurality of staining vessels 20 and the process of an identical step may be shared by the plurality of staining vessels 20. In the present embodiment, the fourth staining vessel 20d and the fifth staining vessel 20e are the staining vessels that store an identical kind of the staining liquid 11 and that perform the process of an identical step. In this case, the total number of the insertion regions 12 of the fourth staining vessel 20d and the fifth staining vessel 20e is preferably set to be B/A or greater. The glass slides 10 are transferred to either one of the fourth staining vessel 20d and the fifth staining vessel 20e, and are not transferred to the other of the fourth staining vessel 20d and the fifth staining vessel 20e. With this configuration, even when the staining liquid 11 of one of the fourth staining vessel 20d and the fifth staining vessel 20e is replaced, the staining process can be continued in the other of the fourth staining vessel 20d and the fifth staining vessel 20e.

Here, when the number of first holders 21 becomes large, the volume of the staining vessel 20 is increased, accordingly, and the amount of the staining liquid stored therein is also increased. Thus, the time period necessary for replacing the staining liquid 11 is increased. Meanwhile, in the present invention, since a plurality of staining vessels (the fourth staining vessel 20d and the fifth staining vessel 20e) that perform an identical step are provided, increase in the waiting time for replacing the staining liquid 11 can be suppressed.

With reference back to FIG. 2, the drying vessel 50 is disposed so as to be aligned with the staining vessels 20 and the washing vessels 40 in the arrangement direction Y thereof. The drying vessel 50 is adjacent to the structure 14. The drying vessel 50 is provided in order to dry the glass slides 10 having been subjected to the staining process and the washing process. The drying vessel 50 includes a plurality of third holders 51 configured to hold glass slides 10. The plurality of third holders 51 have open upper ends, and are arranged with an interval therebetween in the Y direction. The third holders 51 can hold the glass slides 10 one by one with an interval therebetween. Inside the drying vessel 50, an air passage (not shown) is provided, and the air passage is connected to the air-sending unit 60. The transfer unit 30 is configured to put in/take out the glass slides 10 one by one with respect to the third holders 51 of the drying vessel 50.

The air-sending unit 60 is provided in order to send air to the glass slides 10 held in the drying vessel 50. The air-sending unit 60 includes an electric fan, for example, and can forcibly send air into the air passage inside the drying vessel 50. The air-sending unit 60 can dry the glass slides 10 by continuously sending air, for a predetermined time period, to the glass slides 10 set in the third holders 51 inside the drying vessel 50. Since the drying vessel 50 and the air-sending unit 60 are provided, the glass slides 10 having been subjected to the staining process can be speedily dried, and thus, the time period necessary for the staining process can be shortened. Similarly to the staining vessel 20 and the washing vessel 40, the glass slide 10 can be inserted and pulled out with respect to the third holders 51 by the transfer unit 30, and thus, the configuration of the apparatus can be simplified.

Preferably, the smear preparation apparatus 100 includes a heater 52 which warms the air sent from the air-sending unit 60. The heater 52 is located between the air-sending unit 60 and the drying vessel 50. The air sent from the air-sending unit 60 receives heat when passing through the heater 52, and then is sent in a state of warm air having an increased temperature, to the air passage in the drying vessel 50. Accordingly, the glass slides 10 having been subjected to the staining process can be more speedily dried, and thus, the time period necessary for the staining process can be further shortened.

The first transfer unit 30a and the second transfer unit 30b of the transfer unit 30 are both disposed above (Z1 direction) the staining vessels 20 and the washing vessels 40. The first transfer unit 30a and the second transfer unit 30b can each be moved in the horizontal direction (i.e., X direction and Y direction) by a movement mechanism 32.

The movement mechanism 32 includes: a Y axis rail 33a and a Y axis slider 33b in the Y direction; an X axis rail 34a and an X axis slider 34b in the X direction; and a Y axis motor 33c and an X axis motor 34c. As each of the X axis motor 34c and the Y axis motor 33c, a stepping motor or a servo motor can be employed, for example.

The Y axis rail 33a linearly extends in the Y direction, and is fixed to the lower face of the support member 33d. The support member 33d is, for example, a ceiling portion or a support beam member of the housing of the smear preparation apparatus 100. The Y axis slider 33b is mounted to the lower face side (Z2 direction side) of the Y axis rail 33a, and can move along the Y axis rail 33a. The Y axis motor 33c causes the Y axis slider 33b to move in the Y direction via a transmission mechanism not shown. As the transmission mechanism, a belt pulley mechanism or a rack-and-pinion mechanism can be employed, for example.

The X axis rail 34a linearly extends in the X direction and is fixed to the lower face of the Y axis slider 33b. The X axis slider 34b is mounted to the lower face side (Z2 direction side) of the X axis rail 34a, and can move along the X axis rail 34a. The X axis motor 34c causes the X axis slider 34b to move in the X direction via a transmission mechanism not shown.

The Y axis slider 33b, the X axis rail 34a, the X axis slider 34b, the X axis motor 34c, and the Y axis motor 33c are each provided in a pair. At the lower face sides of the pair of the X axis sliders 34b, the first transfer unit 30a and the second transfer unit 30b are mounted, respectively. Accordingly, the first transfer unit 30a and the second transfer unit 30b can move in the X direction independently of each other, along the separate X axis rails 34a. In addition, the first transfer unit 30a and the second transfer unit 30b can move in the Y direction independently of each other, along the common Y axis rail 33a.

The configuration of the first transfer unit 30a and the configuration of the second transfer unit 30b are common to each other. The first transfer unit 30a and the second transfer unit 30b each include a Z axis motor 35a and a transmission mechanism 35b for raising and lowering the hand 31. The Z axis motor 35a causes the hand 31 to be raised and lowered via the transmission mechanism 35b. As the transmission mechanism 35b, a belt pulley mechanism or a rack-and-pinion mechanism can be employed, for example.

Figure 5:
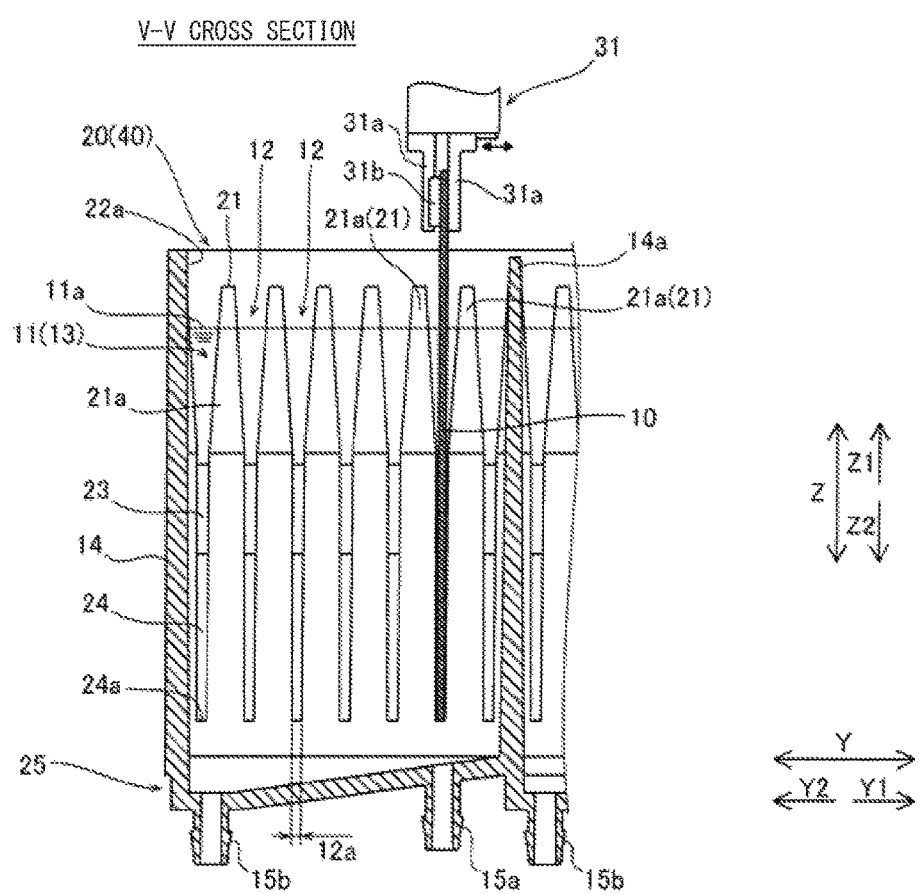
FIG. 5 is a partial sectional view taken along the line V-V shown in FIG. 4.

The hand 31 can grasp one glass slide 10. FIG. 5 shows an example of a configuration in which a glass slide 10 is nipped and grasped in the thickness direction thereof by a pair of grasping plates 31a. As shown in FIG. 5, the pair of grasping plates 31a can nip a glass slide 10 by being in contact with the front surface side and the rear surface side of the glass slide 10. Of the pair of grasping plates 31a, the grasping plate 31a at the rear surface side (Y1 direction side) can move in the thickness direction of the glass slide 10. Moving of the grasping plate 31a can be performed by using an actuator such as an air cylinder, a motor, or a solenoid, for example, but illustration and description thereof are omitted. The hand 31 may be configured to nip and grasp a glass slide 10 in the width direction.

Preferably, a cushion member 31b formed from a flexible material such as rubber is provided to the grasping plate 31a at the front surface side (Y2 direction side) of the glass slide 10. Accordingly, when the grasping plate 31a is to grasp the glass slide 10, even if the grasping plate 31a comes into contact with a print provided at the front surface of the glass slide 10, readability of the print is suppressed from being impaired. A cushion member similar to the cushion member 31b may be provided to the grasping plate 31a at the rear surface side.

With reference back to FIG. 2, the first transfer unit 30a can move to positions above the first staining vessel 20a, the second staining vessel 20b, the third staining vessel 20c, and the first washing vessel 40a on the Y2 direction side. Therefore, the first transfer unit 30a can insert and pull out the glass slides 10 one by one with respect to the insertion regions 12 of each of the first staining vessel 20a, the second staining vessel 20b, the third staining vessel 20c, and the first washing vessel 40a.

The second transfer unit 30b can move among positions above the second washing vessel 40b, the fifth staining vessel 20e, the fourth staining vessel 20d, and the first washing vessel 40a on the Y1 direction side, a position above the drying vessel 50, and a transfer position to a slide storage unit 86 (see FIG. 6) described later. Therefore, the second transfer unit 30b can insert and pull out the glass slides 10 one by one with respect to the insertion regions 12 of each of the fourth staining vessel 20d, the fifth staining vessel 20e, the first washing vessel 40a, and the second washing vessel 40b.

The first transfer unit 30a and the second transfer unit 30b can transfer, in parallel, different glass slides 10, respectively. The operation range of the first transfer unit 30a and the operation range of the second transfer unit 30b overlap each other at the first washing vessel 40a, and in the first washing vessel 40a, the glass slide 10 is handed over. The handing over position may be a position other than the first washing vessel 40a.

Details of Configuration of Staining Vessel and Washing Vessel

Next, details of configurations of the staining vessel 20 and the washing vessel 40 in a preferable embodiment are described. As described above, the structures of individual staining vessels 20 and individual washing vessels 40 are basically the same, except for the number of first holders 21 or the number of second holders 41. Thus, in the following, the structure of one staining vessel 20 is described in detail.

Figure 4:
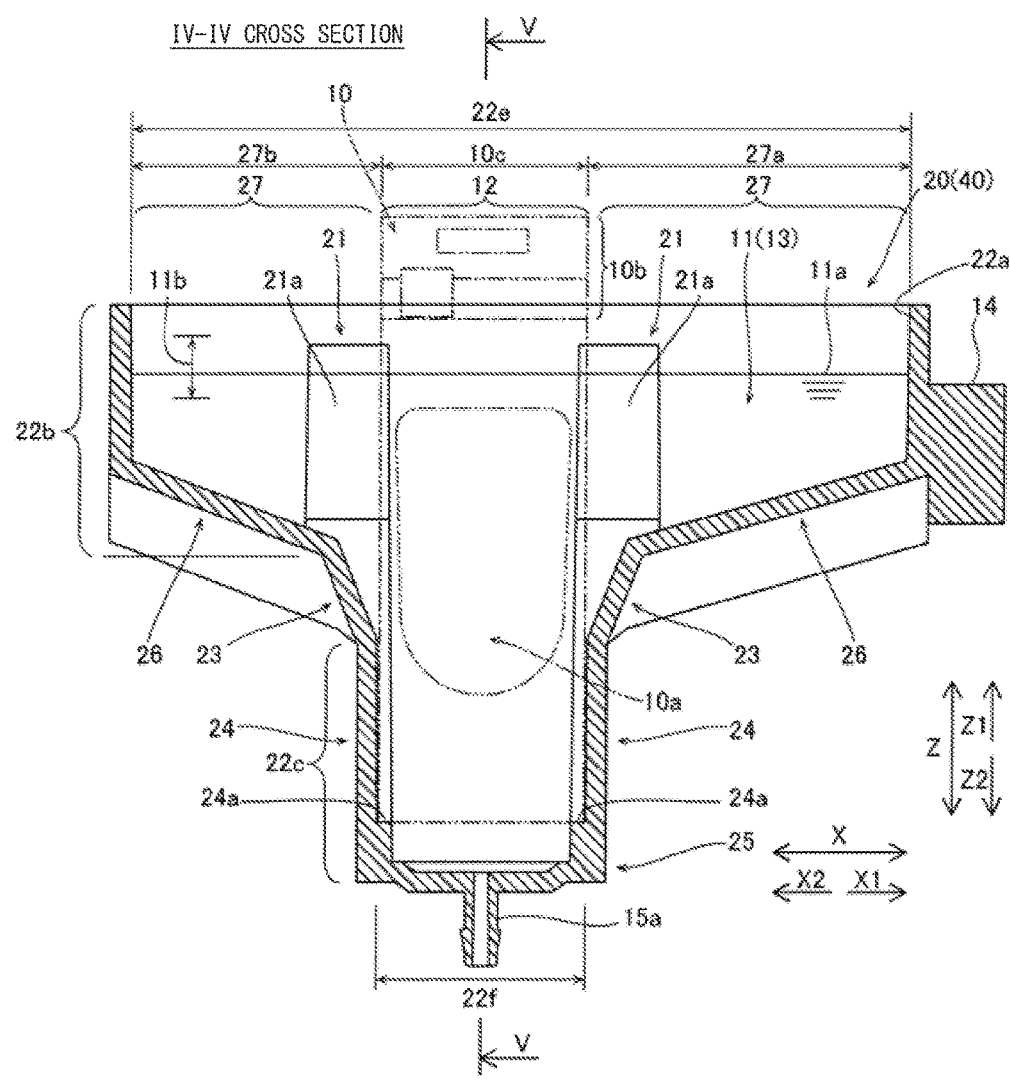
FIG. 4 is an enlarged longitudinal cross-sectional view taken along the line IV-IV shown in FIG. 3.

As shown in FIG. 4, the staining vessel 20 includes an upper face opening 22a that allows a glass slide 10 to be inserted therethrough, and the glass slide 10 can be inserted or pulled out in the up-down direction Z through the upper face opening 22a. In the staining vessel 20, the cross-sectional shape along the width direction (X direction) of the glass slide 10 (i.e., insertion region 12) is substantially in a T-shape. In the thickness direction (Y direction) of the glass slide 10, the staining vessel 20 basically extends while having the cross-sectional shape shown in FIG. 4 except for a bottom portion thereof.

Here, the shape of the glass slide 10 is described. The glass slide 10 is a rectangular plate-like member. The glass slide 10 includes, in a center portion in the longitudinal direction thereof, a staining region 10a where a sample is smeared. In addition, the glass slide 10 includes a frost part 10b serving as a printing region for sample information, on the front surface of one end portion in the longitudinal direction of the glass slide 10. The frost part 10b is a portion that has been processed to be printable by being coated with a resin material or the like. On the frost part 10b, a sample number, a date, a barcode or two-dimensional code, and the like can be printed. The glass slide 10 is inserted into the staining vessel 20 with the frost part 10b located at the upper side, so as to prevent the frost part 10b from being immersed in the staining liquid 11.

Preferably, in the width direction (X direction) of the glass slide 10, an internal dimension 22e of an upper portion 22b of the staining vessel 20 is greater than an internal dimension 22f of a lower portion 22c of the staining vessel 20. Here, a length 22d (see FIG. 3) in the Y direction of the staining vessel 20 is the same between the upper portion 22b and the lower portion 22c, and the horizontal cross-sectional area is determined depending on the width (internal dimension) in the X direction. Thus, the staining vessel 20 is formed such that the horizontal cross-sectional area in the upper portion 22b is greater than the horizontal cross-sectional area in the lower portion 22c. This can suppress the variation in the liquid level of the staining liquid 11 in the upper portion 22b, the variation being caused by decrease of the staining liquid and associated with putting in/taking out the glass slide 10.

That is, the supply amount of the staining liquid 11 is set such that a liquid surface position 11a is above the staining region 10a of the glass slide 10 and is located below the frost part 10b, in a state where the glass slide 10 is inserted. However, the liquid surface position 11a goes up or down within a variation range 11b, in accordance with the number of glass slides 10 inserted in the staining vessel 20. Therefore, by setting the horizontal cross-sectional area in the upper portion 22b to be relatively large, it is possible to decrease the variation range 11b associated with increase and decrease of the number of inserted glass slides 10. As a result, even when the number of glass slides 10 varies, the staining region 10a can be reliably stained. On the other hand, if the horizontal cross-sectional area of the lower portion 22c is also set to be large, the stored amount of the staining liquid 11 for locating the liquid surface position 11a at a predetermined height is increased, and thus, the consumption amount of the staining liquid 11 is increased. Therefore, by setting the horizontal cross-sectional area in the lower portion 22c to be relatively small, it is possible to suppress unnecessary increase of the consumption amount of the staining liquid 11.

Preferably, the staining vessel 20 includes an inclined portion 23 between the upper portion 22b and the lower portion 22c in the width direction X of the glass slide 10. The inclined portion 23 is inclined in a direction along which the width is reduced toward the lower portion 22c. Specifically, the inclined portion 23 is linearly inclined such that the width (internal dimension) between both sides of the insertion region 12 is reduced toward the lower side (Z2 direction). The inclined portion 23 may be inclined in a curved manner.

Due to the inclined portion 23, even when the position in the X direction of the glass slide 10 is slightly shifted during insertion of the glass slide 10, the glass slide 10 can be reliably inserted into the lower portion 22c.

The lower portion 22c includes a lateral support portion 24 and a bottom portion 25. The lateral support portion 24 is connected, at the upper end thereof, to the lower end of the inclined portion 23, and has a width (internal dimension) substantially equal to a width 10c of the glass slide 10, in the width direction X of the glass slide 10. The lateral support portion 24 has a function of supporting side end faces of the glass slide 10.

Between the lateral support portion 24 and the bottom portion 25, a lower support portion 24a having a step-like shape is present. The lower support portion 24a is located at an upper position relative to the inner bottom face of the bottom portion 25, and protrudes inwardly from the inner face of the lateral support portion 24. The lower support portion 24a is the lower end of the insertion region 12, and the lower support portion 24a can support the lower end face of the inserted glass slide 10. The glass slide 10 is supported at a position that is above and separated from the inner bottom face of the bottom portion 25 of the staining vessel 20.

As shown in FIG. 5, the bottom portion 25 of the staining vessel 20 includes a supply port 15a and a discharge port 15b. The inner bottom face of the bottom portion 25 is formed as an inclined surface, and the discharge port 15b is located at the lowest position in the bottom portion 25. The supply port 15a is located at an upper position relative to the discharge port 15b. Accordingly, when the staining liquid 11 is discharged, the staining liquid 11 gathers at the discharge port 15b, and thus, the staining liquid 11 can be suppressed from remaining in the staining vessel 20.

With reference back to FIG. 4, preferably, the plurality of the first holders 21 are provided in pairs at both end portions in the width direction X of the insertion region 12. Each pair of first holders 21 are not provided at the center portion in the width direction X of the insertion region 12, and inner end portions in the X direction of the pair of first holders 21 overlap, in the Y direction, both end portions in the X direction of the glass slide 10 inserted in the insertion region 12. These overlapping portions are at the outer sides relative to the staining region 10a of the glass slide 10. Therefore, each pair of first holders 21 do not come into contact with the staining region 10a of the glass slide 10 inserted in the insertion region 12, and can respectively support, in the Y direction, both end portions in the X direction of the glass slide 10.

As shown in FIG. 5, the plurality of the first holders 21 are arranged with an interval 12a therebetween, the interval 12a corresponding to the insertion region 12 in the thickness direction Y of the insertion region 12. The first holders 21 can support, from both sides in the Y direction, both end portions in the X direction of the glass slide 10.

Preferably, in the thickness direction (Y direction) of the glass slide 10, at least a part of the first holder 21 is tapered toward the upper end thereof. That is, the first holder 21 includes a tapered portion 21*a* which is tapered toward the upper end thereof in the Y direction. The tapered portion 21*a* functions as a guide in the Y direction when the glass slide 10 is to be inserted. Due to the tapered portion 21*a*, even when the position in the Y direction of the glass slide 10 is slightly shifted during insertion of the glass slide 10, the glass slide 10 can be reliably inserted into the insertion region 12.

Transfer Path of Transfer Unit

Next, the path along which the glass slide 10 is transferred by the transfer unit 30 according to a preferable embodiment is described.

As shown in FIG. 3, preferably, the transfer unit 30 transfers the glass slide 10 by making a detour such that the glass slide 10 does not pass above the first holders 21. In the example shown in FIG. 3, the transfer unit 30 transfers the glass slide 10 along the path 27*c*. That is, since the first holders 21 are disposed side by side in the Y direction, the transfer unit 30 transfers the grasped glass slide 10 in the Y direction, at a position shifted in the X direction relative to the first holders 21. Then, the transfer unit 30 aligns the position in the Y direction of the grasped glass slide 10 with the position in the Y direction of the first holders 21 which is the transfer destination, and then moves the glass slide 10 in the X direction, to locate the glass slide 10 above the insertion region 12. Thus, even if the staining liquid 11 attached to the glass slide 10 drops during the transfer of the glass slide 10, the droplets of the dropped staining liquid 11 can be prevented from attaching to the frost part 10*b* of another glass slide 10. As a result, portions other than the staining region of the glass slide 10 can be prevented from being smudged by the staining liquid 11.

The staining vessel 20 includes a transfer region 27 adjacent to the first holders 21, in the width direction X of the glass slide 10. The transfer unit 30 transfers the glass slide 10 such that the glass slide 10 passes above the transfer region 27.

As shown in FIG. 4, the transfer region 27 is present at both sides in the X direction relative to a pair of first holders 21. The transfer regions 27 at both sides respectively have a width 27*a* and a width 27*b* which are each greater than the width 10*c* of the glass slide 10. In the transfer regions 27, the staining liquid 11 is stored similarly to the insertion region 12. In the example shown in FIG. 4, the transfer regions 27 are formed, in the upper portion 22*b* having the internal dimension 22*e*, by a protruding portion 26 formed so as to protrude in the X direction from the inclined portion 23. In other words, the transfer regions 27 are formed as a result of the internal dimension 22*e* of the upper portion 22*b* being made greater than the internal dimension 22*f* of the lower portion 22*c*. As shown in FIG. 3, the transfer unit 30 transfers the glass slide 10 along the path 27*c* that passes above the transfer region 27. Thus, the staining liquid 11 attached to the grasped glass slide 10 is prevented from dropping to the outside of the staining vessel 20. That is, the transfer region 27 of the staining vessel 20 functions as a receiver of the staining liquid 11 that drops during transfer of the glass slide 10. As a result, decrease of the staining liquid 11 in the staining vessel 20 can be suppressed, and smudging of the outside of the staining vessel 20 by the dropped staining liquid 11 can be inhibited.

More preferably, the staining vessel 20 and the washing vessel 40 are adjacent to each other. In addition, the transfer unit 30 makes a detour such that the glass slide 10 does not pass above the first holders 21 of the staining vessel 20 and the second holders 41 of the washing vessel 40, and transfers the glass slide 10 along the direction in which the staining vessel 20 and the washing vessel 40 are adjacent to each other.

In the example shown in FIG. 3, the staining vessel 20 and the washing vessel 40 are adjacent to each other in the Y direction, and the transfer unit 30 performs transfer above the transfer region 27 along the path 27*c* extending along the Y direction. Thus, even when the transfer unit 30 is caused to make a detour, the transfer unit 30 is simply caused to move along the Y direction in which the staining vessel 20 and the washing vessel 40 are adjacent to each other. Thus, increase in the space necessary for causing the transfer unit 30 to make a detour can be suppressed.

Other Configuration of Smear Preparation Apparatus

Figure 6:
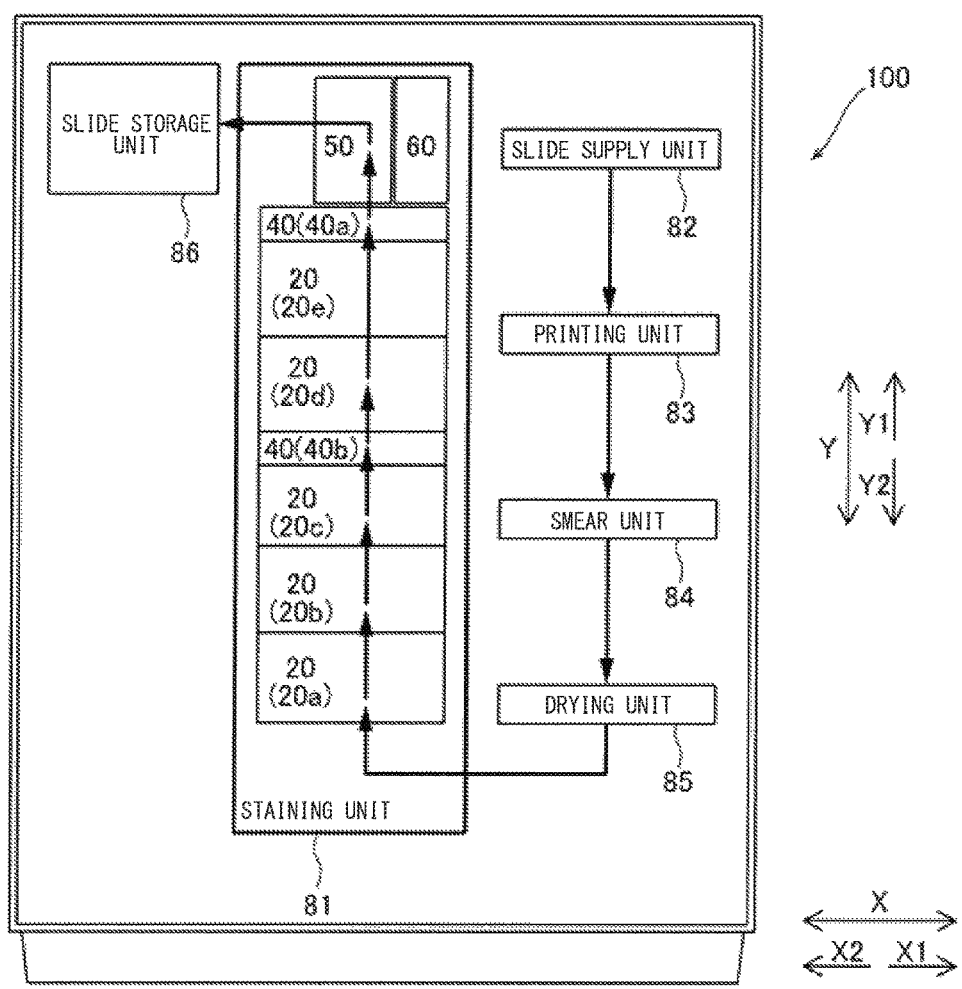
FIG. 6 is a schematic plan view for explaining the overall configuration of the smear preparation apparatus according to one embodiment.

With reference to FIG. 6, other configurations of the smear preparation apparatus 100 are described.

The components such as the staining vessel 20 and the transfer unit 30 shown in FIG. 2 to FIG. 5 are configured as a staining unit 81 shown in FIG. 6. In a preferable embodiment, the smear preparation apparatus 100 further includes a slide supply unit 82, a printing unit 83, a smear unit 84, a drying unit 85, and the slide storage unit 86.

The slide supply unit 82 stores a large number of unused glass slides 10 not yet subjected to sample smearing. The slide supply unit 82 can supply the printing unit 83 with glass slides 10 one by one that have not yet been subjected to smearing.

The printing unit 83 can print various kinds of information such as sample information onto the frost part 10*b* (see FIG. 4) which is the printing region of the glass slide 10. The printing unit 83 can transfer the printed glass slide 10 to the smear unit 84.

The smear unit 84 can suction a sample by means of a sample suction mechanism not shown, and can smear the sample on the staining region 10*a* (see FIG. 4) of the glass slide 10 sent from the printing unit 83. The smear unit 84 can transfer the glass slide 10 having been subjected to the smearing process, to the drying unit 85.

The drying unit 85 has a function of receiving from the smear unit 84 the glass slide 10 having the sample smeared thereon, and of drying the staining region 10*a*.

As described above, in the staining unit 81, each glass slide 10 having a sample smeared thereon and having been dried in the drying unit 85 is subjected to the staining process and the washing process in each of the staining vessel 20 and the washing vessel 40. Thereafter, when a drying step is performed in the drying vessel 50 and staining of the glass slide 10 is completed, the stained glass slide 10 is sent to the slide storage unit 86. Transfer of the glass slide 10 among these units is performed by the transfer unit 30 (see FIG. 2).

The slide storage unit 86 has a function of storing stained glass slides 10.

With this configuration, the smear preparation apparatus 100 can automatically create a smear by performing processes of printing to the glass slide 10, smearing of a sample, and staining.

Staining Operation Performed by Smear Preparation Apparatus

With reference to FIG. 2, FIG. 3, and FIG. 6 to FIG. 9, staining operation performed by the smear preparation apparatus 100 is described. Control of the smear preparation apparatus 100 is performed by the controller 71.

Figure 7:
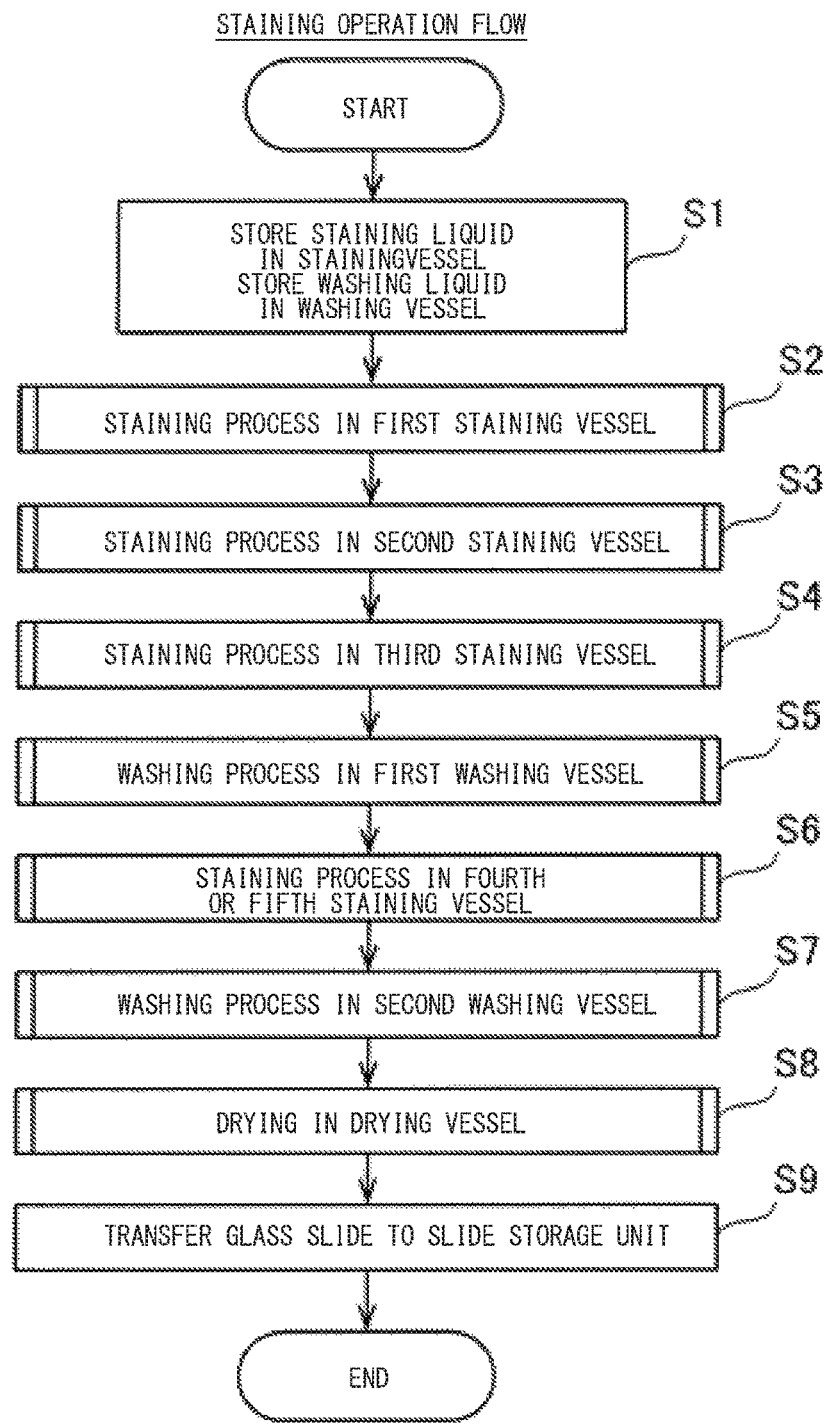
FIG. 7 is a flow chart for explaining the operation performed by the smear preparation apparatus according to one embodiment.

First, in step S1 shown in FIG. 7, the staining liquid 11 and the washing liquid 13 are stored in the staining vessels 20 and the washing vessels 40, respectively. To each staining vessel 20 and each washing vessel 40, the fluid circuit unit 70 (see FIG. 2) supplies the staining liquid 11 and the washing liquid 13 via the supply ports 15*a* (see FIG. 3), respectively.

In step S2, the transfer unit 30 transfers the glass slides 10 one by one to the first staining vessel 20*a* (see FIG. 3), and a staining process is performed in the first staining vessel 20*a*.

Figure 8:
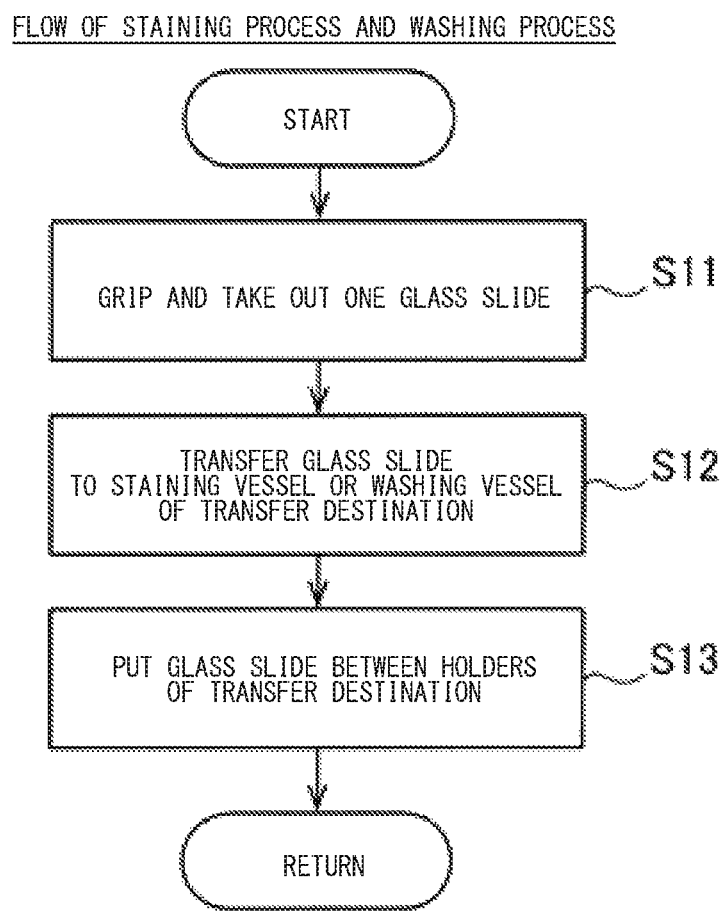
FIG. 8 is a flow chart of a staining process and a washing process shown in FIG. 7.

Specifically, in step S11 shown in FIG. 8, the transfer unit 30 grips and takes out one smeared glass slide 10. In step S12, the transfer unit 30 transfers the glass slide 10 to a position above the first staining vessel 20*a* which is the transfer destination. At this time, the transfer unit 30 transfers the glass slide 10 along the path 27*c* shown in FIG. 3. In step S13, the transfer unit 30 puts the griped glass slide 10 between first holders 21 of the first staining vessel 20*a* which is the transfer destination. The operation shown in FIG. 8 is common in steps S3 to S7 described later, except that the take-out position and the transfer destination of the glass slide 10 are different.

In the first staining vessel 20*a*, a first staining liquid 11 is stored. In this state, the glass slide 10 is immersed in the first staining liquid 11 for a predetermined set time period T1, whereby the staining process is performed.

With reference back to FIG. 7, in step S3, the transfer unit 30 transfers the glass slide 10 to the second staining vessel 20*b* (see FIG. 3), and a staining process is performed in the second staining vessel 20*b*. Through steps S11 to S13 shown in FIG. 8, the glass slide 10 is taken out of the first staining vessel 20*a* by the transfer unit 30, and is put between first holders 21 of the second staining vessel 20*b*. The glass slide 10 is immersed in a second staining liquid 11 stored in the second staining vessel 20*b*, for a predetermined set time period T2.

In step S4, the transfer unit 30 transfers the glass slide 10 to the third staining vessel 20*c* (see FIG. 3), and a staining process is performed in the third staining vessel 20*c*. Through steps S11 to S13 shown in FIG. 8, the glass slide 10 is taken out of the second staining vessel 20*b* by the transfer unit 30, and is put between first holders 21 of the third staining vessel 20*c*. The glass slide 10 is immersed in a third staining liquid 11 stored in the third staining vessel 20*c*, for a predetermined set time period T3.

In step S5, the transfer unit 30 transfers the glass slide 10 to the first washing vessel 40*a* (see FIG. 3), and a washing process is performed in the first washing vessel 40*a*. Transfer operation to the first washing vessel 40*a* is also similar to the transfer operation to the staining vessel 20. That is, in step S11 shown in FIG. 8, the transfer unit 30 grips and takes out one glass slide 10 from the third staining vessel 20*c*. In step S12, the transfer unit 30 transfers the glass slide 10 along the path 27*c* (see FIG. 3) to a position above the first washing vessel 40*a* which is the transfer destination. In step S13, the transfer unit 30 puts the griped glass slide 10 between second holders 41 of the first washing vessel 40*a* which is the transfer destination. The glass slide 10 is immersed in a first washing liquid 13 stored in the first washing vessel 40*a*, for a predetermined set time period T4.

In step S6, the transfer unit 30 transfers the glass slide 10 to the fourth staining vessel 20*d* or the fifth staining vessel 20*e*, and a staining process is performed in the fourth staining vessel 20*d* or the fifth staining vessel 20*e* (see FIG. 3) whichever is the transfer destination. In the fourth staining vessel 20*d* and the fifth staining vessel 20*e*, the same fourth staining liquid 11 is stored. Through steps S11 to S13 shown in FIG. 8, the glass slide 10 is taken out of the first washing vessel 40*a* by the transfer unit 30, and is put between first holders 21 of the fourth staining vessel 20*d* or the fifth staining vessel 20*e*. The glass slide 10 is immersed in the fourth staining liquid 11 for a predetermined set time period T5.

In step S7, the transfer unit 30 transfers the glass slide 10 to the second washing vessel 40*b* (see FIG. 3), and a washing process is performed in the second washing vessel 40*b*. Through steps S11 to S13 shown in FIG. 8, the glass slide 10 is taken out of the fourth staining vessel 20*d* or the fifth staining vessel 20*e* by the transfer unit 30, and is put between second holders 41 of the second washing vessel 40*b*. The glass slide 10 is immersed in the second washing liquid 13 stored in the second washing vessel 40*b*, for a predetermined set time period T6.

In step S8, the transfer unit 30 transfers the glass slide 10 to the drying vessel 50 (see FIG. 2), and the glass slide 10 is dried in the drying vessel 50.

Figure 9:
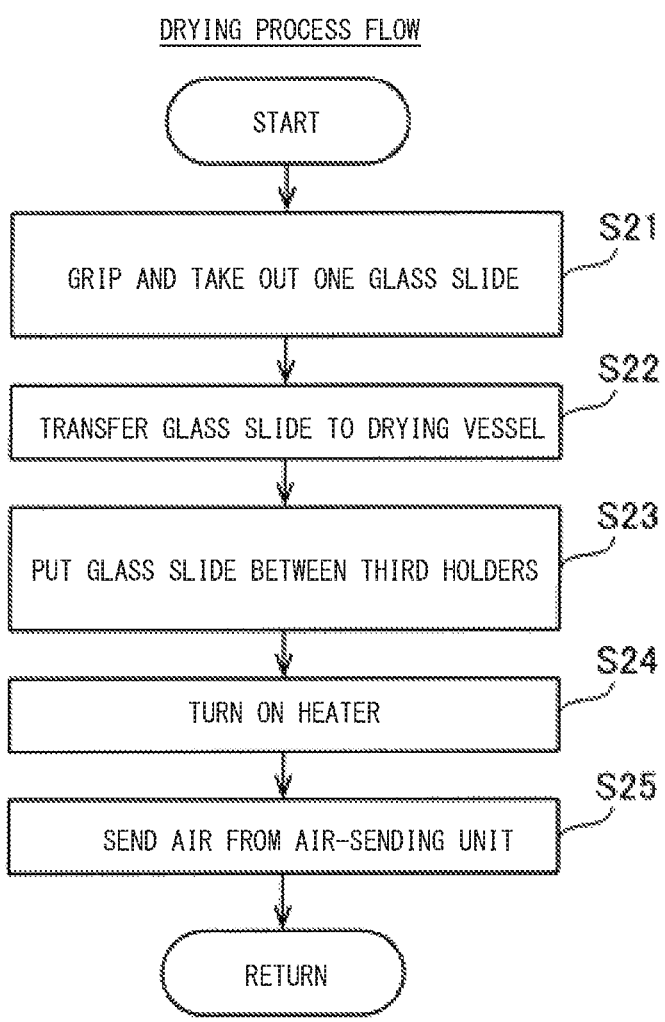
FIG. 9 is a flow chart of a drying process performed in a drying vessel shown in FIG. 7.

Specifically, in step S21 shown in FIG. 9, the transfer unit 30 grips and takes out one glass slide 10 from the second washing vessel 40*b*. In step S22, the transfer unit 30 transfers the glass slide 10 to a position above the drying vessel 50 which is the transfer destination. In step S23, the transfer unit 30 puts the griped glass slide 10 between third holders 51 (see FIG. 2) of the drying vessel 50 which is the transfer destination. In step S24, the controller 71 turns on the heater 52 (see FIG. 2). Then, in step S25, the air-sending unit 60 (see FIG. 2) sends air to the glass slide 10 held in the drying vessel 50. At this time, the heater 52 warms the air sent from the air-sending unit 60. The glass slide 10 receives the air in the drying vessel 50 for a predetermined set time period T7. As a result, the smear staining process onto one glass slide 10 is completed.

With reference back to FIG. 7, in step S9, the transfer unit 30 takes out, from the drying vessel 50, one glass slide 10 for which the staining process has been completed, and transfers the glass slide 10 to the slide storage unit 86. In the manner as described above, the staining operation by the smear preparation apparatus 100 is performed.

Operation Performed by First Transfer Unit and Second Transfer Unit

Since the first transfer unit 30*a* and the second transfer unit 30*b* perform the transfer of glass slides 10 in parallel, operations performed by the first transfer unit 30*a* and the second transfer unit 30*b* in the above-described staining operation are described in detail. Control of the first transfer unit 30*a* and the second transfer unit 30*b* in the staining processing operation is performed by the controller 71.

Operation Performed by First Transfer Unit

First, operation performed by the first transfer unit 30*a* is described. In step S31 shown in FIG. 10, the controller 71 determines whether or not a smeared glass slide 10 is present. When the smeared glass slide 10 is present, the first transfer unit 30a transfers, in step S32, the smeared glass slide 10 to the first staining vessel 20a. For each of the glass slides 10 to be processed, the controller 71 counts the elapsed time period from the time point when the transfer of the glass slide 10 has been completed.

Figure 10:
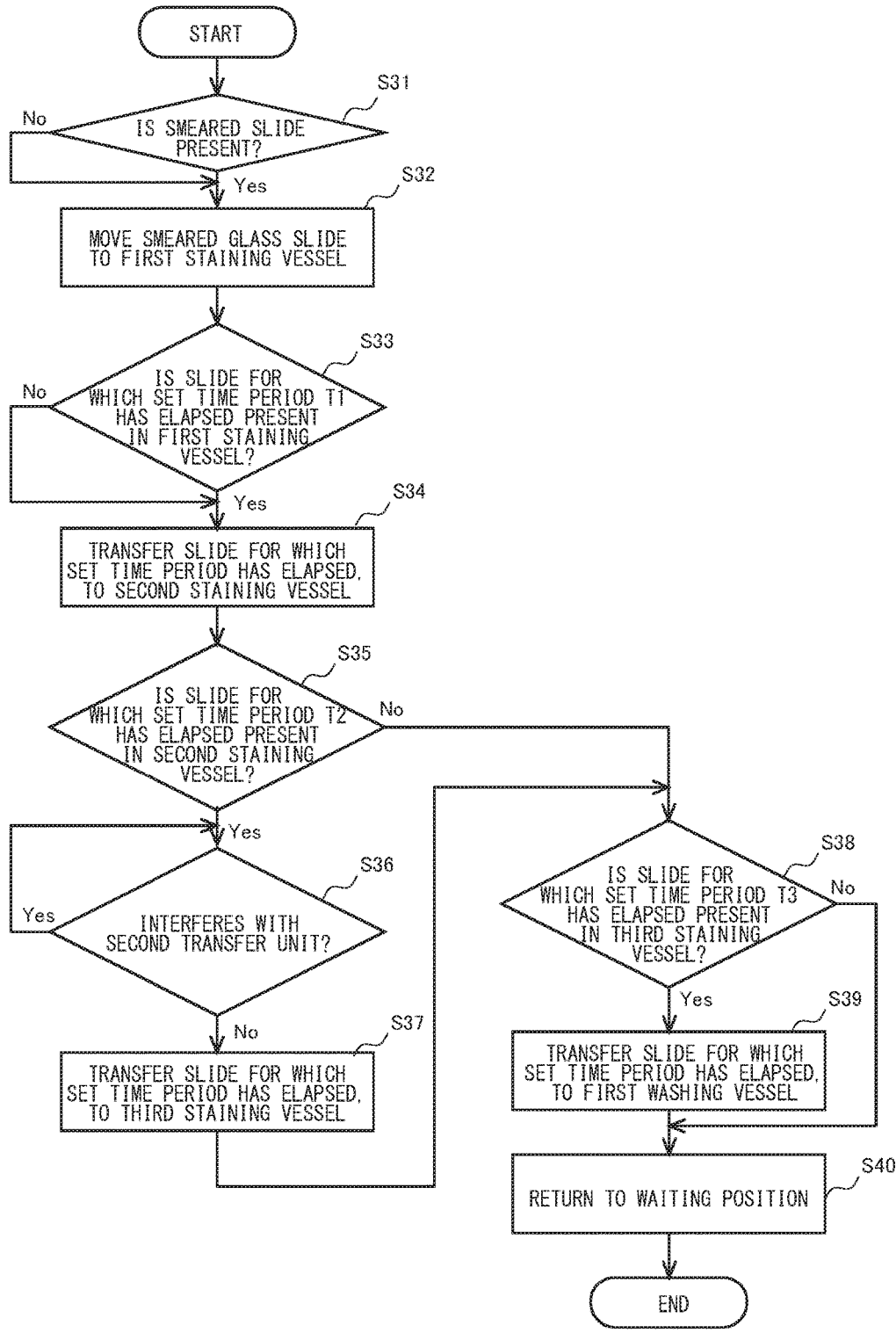
FIG. 10 is a flow chart for explaining the operation performed by a first transfer unit.

In step S33 shown in FIG. 10, the controller 71 determines whether or not a glass slide 10 for which the set time period T1 has elapsed is present in the first staining vessel 20a. The set time period T1 is 120 seconds, for example. When the glass slide 10 for which the set time period T1 has elapsed is present in the first staining vessel 20a, the process is advanced to step S34, and the first transfer unit 30a transfers, to the second staining vessel 20b, the glass slide 10 of the first staining vessel 20a for which the set time period T1 has elapsed.

In step S35, the controller 71 determines whether or not a glass slide 10 for which the set time period T2 has elapsed is present in the second staining vessel 20b. The set time period T2 is 300 seconds, for example. When the glass slide 10 for which the set time period T2 has elapsed is present in the second staining vessel 20b, the process is advanced to step S36.

In step S36, the controller 71 determines whether or not the first transfer unit 30a interferes with the second transfer unit 30b. Specifically, the controller 71 determines whether or not the second transfer unit 30b is present in an interference range which is set to a range that includes the first washing vessel 40a which is the operation overlapping region between the second transfer unit 30b and the first transfer unit 30a. When the second transfer unit 30b is present in the interference range, the controller 71 repeats the determination of step S36, and waits until the second transfer unit 30b comes out of the interference range. When the controller 71 has determined that the first transfer unit 30a does not interfere with the second transfer unit 30b (i.e., the second transfer unit 30b is not present in the interference range), the controller 71 advances the process to step S37.

In step S37, the first transfer unit 30a transfers, to the third staining vessel 20c, the glass slide 10 of the second staining vessel 20b for which the set time period T2 has elapsed. In step S38, the controller 71 determines whether or not a glass slide 10 for which the set time period T3 has elapsed is present in the third staining vessel 20c. The set time period T3 is 300 seconds, for example. When the glass slide 10 for which the set time period T3 has elapsed is present in the third staining vessel 20c, the process is advanced to step S39.

In step S39, the first transfer unit 30a transfers, to the first washing vessel 40a, the glass slide 10 of the third staining vessel 20c for which the set time period T3 has elapsed. In step S40, the first transfer unit 30a returns to a predetermined waiting position.

Meanwhile, when the controller 71 has determined in step S31 that the smeared glass slide 10 is not present, the controller 71 advances the process to step S33. When the controller 71 has determined in step S33 that the glass slide 10 for which the set time period T1 has elapsed is not present in the first staining vessel 20a, the controller 71 advances the process to step S35. In step S35, when the controller 71 has determined that the glass slide 10 for which the set time period T2 has elapsed is not present in the second staining vessel 20b, the controller 71 advances the process to step S38. In step S38, when the controller 71 has determined that the glass slide 10 for which the set time period T3 has elapsed is not present in the third staining vessel 20c, the controller 71 advances the process to step S40.

As described above, in each of steps S31, S33, S35, and S38, the controller 71 determines the presence/absence of a glass slide 10 that should be transferred, and when there is no glass slide 10 that should be transferred, the controller 71 returns the first transfer unit 30a to the waiting position. When there is a smeared glass slide 10 or a glass slide 10 for which a set time period has elapsed, the glass slide 10 is sent to the next step.

Operation Performed by Second Transfer Unit

Figure 11:
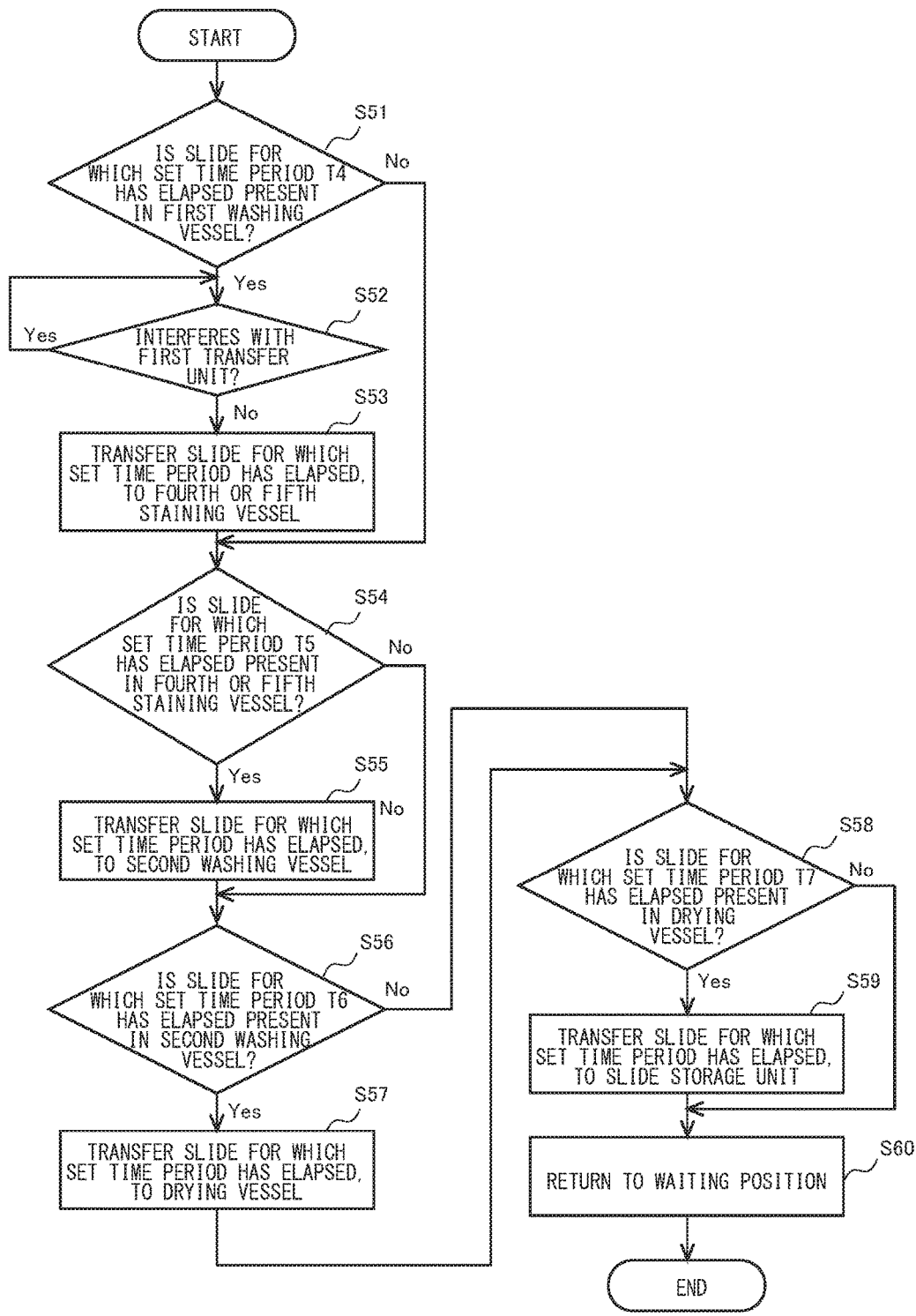
FIG. 11 is a flow chart for explaining the operation performed by a second transfer unit.

Next, operation performed by the second transfer unit 30b is described. In step S51 shown in FIG. 11, the controller 71 determines whether or not a glass slide 10 for which the set time period T4 has elapsed is present in the first washing vessel 40a. The set time period T4 is 15 seconds, for example. When the glass slide 10 for which the set time period T4 has elapsed is present in the first washing vessel 40a, the process is advanced to step S52.

In step S52, the controller 71 determines whether or not the second transfer unit 30b interferes with the first transfer unit 30a. Similarly to step S36 shown in FIG. 10, the controller 71 determines whether or not the first transfer unit 30a is present in the interference range. When the controller 71 has determined that the second transfer unit 30b does not interfere with the first transfer unit 30a (i.e., the first transfer unit 30a is not present in the interference range), the controller 71 advances the process to step S53.

In step S53, the second transfer unit 30b transfers, to the fourth staining vessel 20d or the fifth staining vessel 20e, the glass slide 10 of the first washing vessel 40a for which the set time period T4 has elapsed.

In step S54, the controller 71 determines whether or not a glass slide 10 for which the set time period T5 has elapsed is present in the fourth staining vessel 20d or the fifth staining vessel 20e. The set time period T5 is 1200 seconds, for example. When the glass slide 10 for which the set time period T5 has elapsed is present in the fourth staining vessel 20d or the fifth staining vessel 20e, the process is advanced to step S55, and the second transfer unit 30b transfers to the second washing vessel 40b the glass slide 10 for which the set time period T5 has elapsed.

In step S56, the controller 71 determines whether or not a glass slide 10 for which the set time period T6 has elapsed is present in the second washing vessel 40b. The set time period 16 is 60 seconds, for example. When the glass slide 10 for which the set time period T6 has elapsed is present in the second washing vessel 40b, the process is advanced to step S57, and the second transfer unit 30b transfers to the drying vessel 50 the glass slide 10 of the second washing vessel 40b for which the set time period T6 has elapsed.

In step S58, the controller 71 determines whether or not a glass slide 10 for which the set time period T7 has elapsed is present in the drying vessel 50. The set time period T7 is 420 seconds, for example. When the glass slide 10 for which the set time period T7 has elapsed is present in the drying vessel 50, the process is advanced to step S59, and the second transfer unit 30b transfers to the slide storage unit 86 the glass slide 10 for which the set time period T7 has elapsed in the drying vessel 50. Then, in step S60, the second transfer unit 30b returns to a predetermined waiting position. The waiting position for the second transfer unit 30b is a predetermined position outside the interference range.

Meanwhile, when the controller 71 has determined in step S51 that the glass slide 10 for which the set time period T4 has elapsed is not present in the first washing vessel 40a, the controller 71 advances the process to step S54. When the controller 71 has determined in step S54 that the glass slide 10 for which the set time period T5 has elapsed is not present in the fourth staining vessel 20d or the fifth staining vessel 20e, the controller 71 advances the process to step S56. In step S56, when the controller 71 has determined that the glass slide 10 for which the set time period T6 has elapsed is not present in the second washing vessel 40b, the controller 71 advances the process to step S58. In step S58, when the controller 71 has determined that the glass slide 10 for which the set time period T7 has elapsed is not present in the drying vessel 50, the controller 71 advances the process to step S60.

Thus, in each of steps S51, S54, S56, and S58, the controller 71 determines the presence/absence of a glass slide 10 that should be transferred, and when there is no glass slide 10 that should be transferred, the controller 71 returns the second transfer unit 30b the predetermined waiting position.

In the manner as described above, the first transfer unit 30a and the second transfer unit 30b perform transfer of the glass slide 10 in parallel.

It should be noted that the embodiment disclosed herein is merely illustrative in all aspects and should not be construed as being restrictive. The scope of the present invention is defined not by the description of the above embodiment but by the scope of the claims, and includes meaning equivalent to the scope of the claims and all modifications within the scope.

What is claimed is:

1. A smear preparation apparatus comprising:
   a smearing unit configured to smear samples on respective glass slides;
   a staining vessel comprising:
      a first staining vessel configured to store a first staining liquid for staining a sample, and comprising first holders, each configured to hold one of the glass slides on which a sample is smeared; and
      a second staining vessel configured to store a second staining liquid for staining the sample, and comprising second holders, each configured to hold the one of the glass slides on which the sample is smeared, the second staining liquid being different from the first staining liquid; and
   a transfer unit configured to transfer the glass slides one by one from the smearing unit to the first holders to stain the glass slides one by one in the first staining vessel, and to transfer the glass slides one by one from the first holders to the second holders to stain the glass slides one by one in the second staining vessel.

2. The smear preparation apparatus of claim 1, wherein
   the first holders are provided side by side in a predetermined direction, and
   the transfer unit transfers in the predetermined direction a glass slide having been subjected to a staining process, by making a detour such that the glass slide having been subjected to the staining process does not pass above a glass slide being subjected to the staining process.

3. The smear preparation apparatus of claim 1, wherein
   the first holders are provided side by side in a thickness direction of the glass slide,
   the staining vessel comprises a transfer region that is adjacent to the first holders in a width direction of the glass slide, and
   the transfer unit transfers the glass slide such that the glass slide passes above the transfer region.

4. The smear preparation apparatus of claim 1, wherein
   in a width direction of the glass slide, an internal dimension of an upper portion of the staining vessel is greater than an internal dimension of a lower portion of the staining vessel.

5. The smear preparation apparatus of claim 1, further comprising:
   a washing vessel for storing a washing liquid therein, wherein
   the washing vessel comprises third holders configured to hold the glass slides one by one in the washing vessel, and
   the transfer unit is configured to put in or take out the glass slides one by one with respect to the third holders of the washing vessel.

6. The smear preparation apparatus of claim 5, wherein
   the staining vessel is formed integrally with the washing vessel.

7. The smear preparation apparatus of claim 5, wherein
   the staining vessel and the washing vessel are adjacent to each other,
   the first holders, the second holders and the third holders are provided side by side in a direction in which the staining vessel, comprising the first staining vessel and the second staining vessel, and the washing vessel are adjacent to each other, and
   the transfer unit makes a detour such that the glass slide does not pass above the first holders, the second holders and the third holders, and transfers the glass slide along the direction in which the staining vessel, comprising the first staining vessel and the second staining vessel, and the washing vessel are adjacent to each other.

8. The smear preparation apparatus of claim 1, wherein
   the staining vessel further comprises a separation member for separating the first staining vessel and the second staining vessel from each other, and
   the first staining vessel is formed integrally with the second staining vessel.

9. The smear preparation apparatus of claim 1, further comprising:
   a drying vessel comprising third holders configured to hold the glass slides one by one in the drying vessel; and
   an air-sending unit for sending air to the glass slides held in the drying vessel, wherein
   the transfer unit is configured to put in/take out the glass slides one by one with respect to the third holders of the drying vessel.

10. The smear preparation apparatus of claim 9, further comprising
    a heater for warming air sent from the air-sending unit.

11. The smear preparation apparatus of claim 1, wherein
    the glass slides are immersed one by one in the first staining liquid in the first staining vessel, and
    the glass slides are immersed one by one in the second staining liquid in the second staining vessel.

12. The smear preparation apparatus of claim 11, wherein
    the glass slides are immersed one by one in the first staining liquid in the first staining vessel for a first set period of time, and
    the glass slides are immersed one by one in the second staining liquid in the second staining vessel for a second set period of time.

13. A smear preparation method comprising:
    smearing, by a smearing unit, samples on respective glass slides;
    storing, in a first staining vessel of a staining vessel, a first staining liquid for staining a sample; the first staining vessel comprising first holders each configured to hold one of the glass slides on which a sample is smeared;

storing, in a second staining vessel of the staining vessel, a second staining liquid for staining the sample, the second staining vessel comprising second holders, each configured to hold the one of the glass slides on which the sample is smeared, the second staining liquid being different from the first staining liquid;

transferring, by a transfer unit, the glass slides one by one from the smearing unit to the first holders to stain the glass slides one by one in the first staining vessel; and transferring, by the transfer unit, the glass slides one by one from the first holders to the second holders to stain the glass slides one by one in the second staining vessel.

14. The smear preparation method of claim 13, wherein the first holders are provided side by side in a predetermined direction; and the transfer unit transfers the glass slide in the predetermined direction by making a detour such that the glass slide does not pass above the first holders.

15. The smear preparation method of claim 13, wherein the first holders are provided side by side in a thickness direction of the glass slide, the staining vessel comprises a transfer region that is adjacent to the first holders in a width direction of the glass slide, and the transfer unit transfers the glass slide such that the glass slide passes above the transfer region.

16. The smear preparation method of claim 13, further comprising:

storing a washing liquid in a washing vessel comprising third holders configured to hold the glass slides one by one;

gripping and transferring, by the transfer unit, each glass slide to the washing vessel; and putting in or taking out the glass slides one by one, by the transfer unit, with respect to the third holders of the washing vessel.

17. The smear preparation method of claim 16, wherein the staining vessel and the washing vessel are adjacent to each other, the first holders, the second holders, and the third holders are provided side by side in a direction in which the staining vessel, comprising the first staining vessel and the second staining vessel, and the washing vessel are adjacent to each other and the transfer unit makes a detour such that the glass slide does not pass above the first holders, the second holders, and the third holders, and transfers the glass slide along the direction in which the staining vessel, comprising the first staining vessel and the second staining vessel, and the washing vessel are adjacent to each other.

18. The smear preparation method of claim 13, wherein the first staining vessel and the second staining vessel is separated from each other by a separation member of the staining vessel, and the transfer unit puts in/takes out the glass slides one by one with respect to each of the first holders of the first staining vessel and the second holders of the second staining vessel.

19. The smear preparation method of claim 13, further comprising:

putting in/taking out the glass slides one by one, by the transfer unit, with respect to third holders of a drying vessel, the third holders being configured to hold the glass slides one by one in the drying vessel; and sending, by an air-sending unit, air to the glass slides held in the drying vessel.

20. The smear preparation method of claim 19, further comprising:

warming, by a heater, air sent from the air-sending unit.

21. The smear preparation method of claim 13, wherein transferring, by the transfer unit, the glass slides one by one from the smearing unit to the first holders to stain the glass slides one by one in the first staining vessel comprises immersing the glass slides one by one in the first staining liquid in the first staining vessel; and transferring, by the transfer unit, the glass slides one by one from the first holders to the second holders to stain the glass slides one by one in the second staining vessel comprises immersing the glass slides one by one in the second staining liquid in the second staining vessel.

22. The smear preparation method of claim 21, wherein immersing the glass slides one by one in the first staining liquid in the first staining vessel comprises immersing the glass slides one by one in the first staining liquid in the first staining vessel for a first set period of time, and immersing the glass slides one by one in the second staining liquid in the second staining vessel comprises immersing the glass slides one by one in the second staining liquid in the second staining vessel for a second set period of time.

23. A smear preparation apparatus comprising:

a smearing unit configured to smear samples on respective glass slides;

a staining vessel comprising:

a first staining vessel configured to store a first staining liquid for staining a sample, and comprising first holders, each configured to hold a glass slide on which a sample is smeared; and a second staining vessel configured to store a second staining liquid for staining a sample, and comprising second holders, each configured to hold a glass slide on which a sample is smeared, the second staining liquid being different from the first staining liquid; and a transfer unit configured to transfer, one by one, the glass slides on which the samples are smeared by the smearing unit to the first holders, and to transfer, one by one, the glass slides having samples stained with the first staining liquid in the first staining vessel to the second holders.

24. The smear preparation apparatus of claim 23, further comprising:

a washing vessel for storing a washing liquid therein, wherein the washing vessel is configured to hold a glass slide in the washing vessel, and the transfer unit is configured to transfer, one by one, the glass slides having samples stained with the second staining liquid in the second staining vessel to the washing vessel.

25. The smear preparation apparatus of claim 24, wherein the staining vessel is formed integrally with the washing vessel.

26. The smear preparation apparatus of claim 24, wherein the staining vessel and the washing vessel are adjacent to each other, the first holders and the second holders are provided side by side in a direction in which the staining vessel, comprising the first staining vessel and the second staining vessel, and the washing vessel are adjacent to each other, and the transfer unit transfers sequentially along the direction the glass slides to the first staining vessel and the second staining vessel, and the washing vessel.

27. The smear preparation apparatus of claim 24, further comprising:

a third staining vessel configured to store a third staining liquid for staining a sample, and comprising third holders, each configured to hold a glass slide on which a sample is smeared, the third staining liquid being different from the first staining liquid and the second staining liquid; and a second transfer unit configured to transfer a glass slide from the washing vessel to one of the third holders.

28. The smear preparation apparatus of claim 27, further comprising:

a fourth staining vessel configured to store a fourth staining liquid for staining a sample, and comprising fourth holders, each configured to hold a glass slide on which a sample is smeared, the fourth staining liquid being different from the first staining liquid, the second staining liquid, and the third staining liquid; wherein the second transfer unit is configured to transfer, one by one, the glass slides having samples stained with the third staining liquid in the third staining vessel to the fourth holders.

29. A smear preparation method comprising:

smearing, by a smearing unit, samples on respective glass slides;

storing, in a first staining vessel of a staining vessel, a first staining liquid for staining a sample, the first staining vessel comprising first holders each configured to hold a glass slide on which a sample is smeared;

storing, in a second staining vessel of the staining vessel, a second staining liquid for staining the sample, the second staining vessel comprising second holders, each configured to hold a glass slide on which a sample is smeared, the second staining liquid being different from the first staining liquid;

transferring, one by one, the glass slides on which the samples are smeared by the smearing unit to the first holders by a transfer unit; and transferring, one by one, the glass slides having samples stained with the first staining liquid in the first staining vessel to the second holders by the transfer unit.

30. The smear preparation method of claim 29, further comprising:

storing a washing liquid in a washing vessel configured to hold a glass slide; and transferring, one by one, the glass slides having samples stained with the second staining liquid in the second staining vessel to the washing vessel by the transfer unit.

31. The smear preparation method of claim 30, further comprising:

storing, in a third staining vessel of a staining vessel, a third staining liquid for staining a sample, the third staining vessel comprising third holders, each configured to hold a glass slide on which a sample is smeared, the third staining liquid being different from the first staining liquid and the second staining liquid; and transferring, by a second transfer unit, the glass slide from the washing vessel to the third holders.

32. The smear preparation method of claim 31, further comprising:

storing, in a fourth staining vessel of a staining vessel, a fourth staining liquid for staining a sample, the fourth staining vessel comprising fourth holders each configured to hold a glass slide on which a sample is smeared, the fourth staining liquid being different from the first staining liquid, the second staining liquid and the third staining liquid; and transferring, one by one, the glass slides having samples stained with the third staining liquid in the third staining vessel to the fourth holders by the second transfer unit.

33. The smear preparation method of claim 29, wherein the first staining vessel and the second staining vessel is separated from each other by a separation member of the staining vessel, and the transfer unit puts in/takes out the glass slides one by one with respect to each of the first holders of the first staining vessel and the second holders of the second staining vessel.

* * * * *